US00PP28404P3

(12) United States Plant Patent
Danziger

(10) Patent No.: US PP28,404 P3
(45) Date of Patent: Sep. 19, 2017

(54) ***CARYOPTERIS* PLANT NAMED 'DCAROCEAN'**

(50) Latin Name: *Caryopteris incana*
Varietal Denomination: DCAROCEAN

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 107 days.

(21) Appl. No.: 14/757,137

(22) Filed: Nov. 23, 2015

(65) Prior Publication Data

US 2017/0150666 P1 May 25, 2017

(51) Int. Cl.
*A01H 5/00* (2006.01)

(52) U.S. Cl.
USPC ..... Plt./226

(58) Field of Classification Search
USPC ..... Plt./226, 263.1
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Caryopteris* cultivar named 'DCAROCEAN' is disclosed, characterized by deep violet flowers and short spacing between inflorescences. The new variety is a *Caryopteris*, normally used for ornamental horticulture purposes.

2 Drawing Sheets

Figure 1:
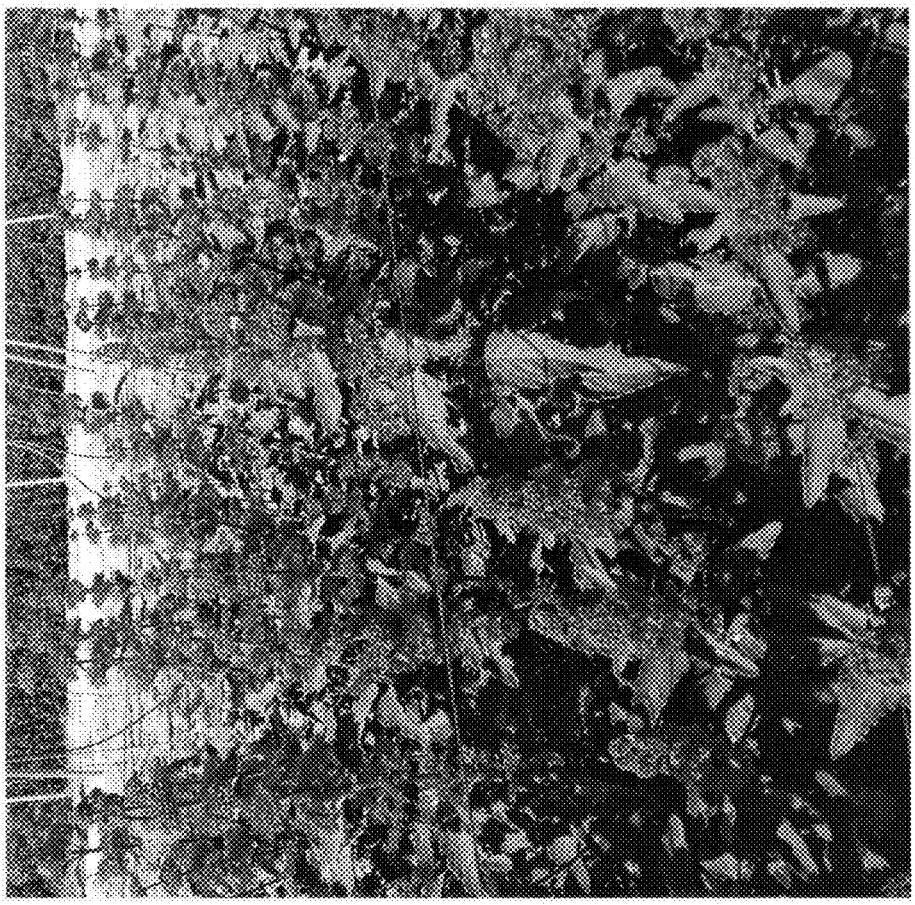

Latin name of the genus and species: *Caryopteris incana*.
Variety denomination: 'DCAROCEAN'.

BACKGROUND OF THE INVENTION

The new *Caryopteris* cultivar is a product of a planned breeding program conducted by the inventor, Gavriel Danziger, in Moshav Mishmar Hashiva, Israel. The objective of the breeding program was to produce new *Caryopteris* varieties for ornamental commercial applications. The open pollination resulting in this new variety was made during August of 2011.

The seed parent is the, unpatented, proprietary variety referred to as *Caryopteris* 'CT-Z-16'. The pollen parent is unknown as it was an open pollination breeding program. The new variety first flowered July of 2012. The new variety was selected August of 2012 by the inventor in a group of seedlings resulting from the 2011 open pollination, in a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel during Fall of 2012 and has shown that the unique features of this cultivar are stable and reproduced true to type in successive generations.

SUMMARY OF THE INVENTION

The cultivar 'DCAROCEAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCAROCEAN' These characteristics in combination distinguish 'DCAROCEAN' as a new and distinct *Caryopteris* cultivar:

1. Deep Violet flowers.
2. Distinctively short space between inflorescences.

Plants of the new cultivar 'DCAROCEAN' are similar to plants of the seed parent, *Caryopteris* 'CT-Z-16' in most horticultural characteristics, however, plants of the new cultivar 'DCAROCEAN' differ in the following;

1. Longer stems than the seed parent.
2. Compact space between inflorescence, whereas the seed parent has elongated space between inflorescence.

COMMERCIAL COMPARISON

Plants of the new cultivar 'DCAROCEAN' are comparable to the unpatented commercial variety *Caryopteris* 'Blue Myth'. The two *Caryopteris* varieties are similar in most horticultural characteristics; however, the new variety 'DCAROCEAN' differs in the following:

1. Shorter spacing between inflorescence.
2. Thicker, harder, quality to stems. The comparator has thinner, softer stems.

Plants of the new cultivar 'DCAROCEAN' can also be comparable to the unpatented commercial variety *Caryopteris* 'Heavenly Blue'. The two *Caryopteris* varieties are similar in most horticultural characteristics; however, the new variety 'DCAROCEAN' differs in the following:

1. Thicker, harder, quality to stems. The comparator has thinner, softer stems.
2. Wide leaves, whereas the comparator has narrow leaves.
3. Violet flowers, whereas the comparator has blueish flowers.

BRIEF DESCRIPTION OF THE PHOTOGRAPHS

The accompanying photograph in FIG. 1 illustrates in full color a typical plant of 'DCAROCEAN' grown outdoors in Israel. Age of the plant photographed is approximately 5 months old from a rooted cutting.

Figure 2:
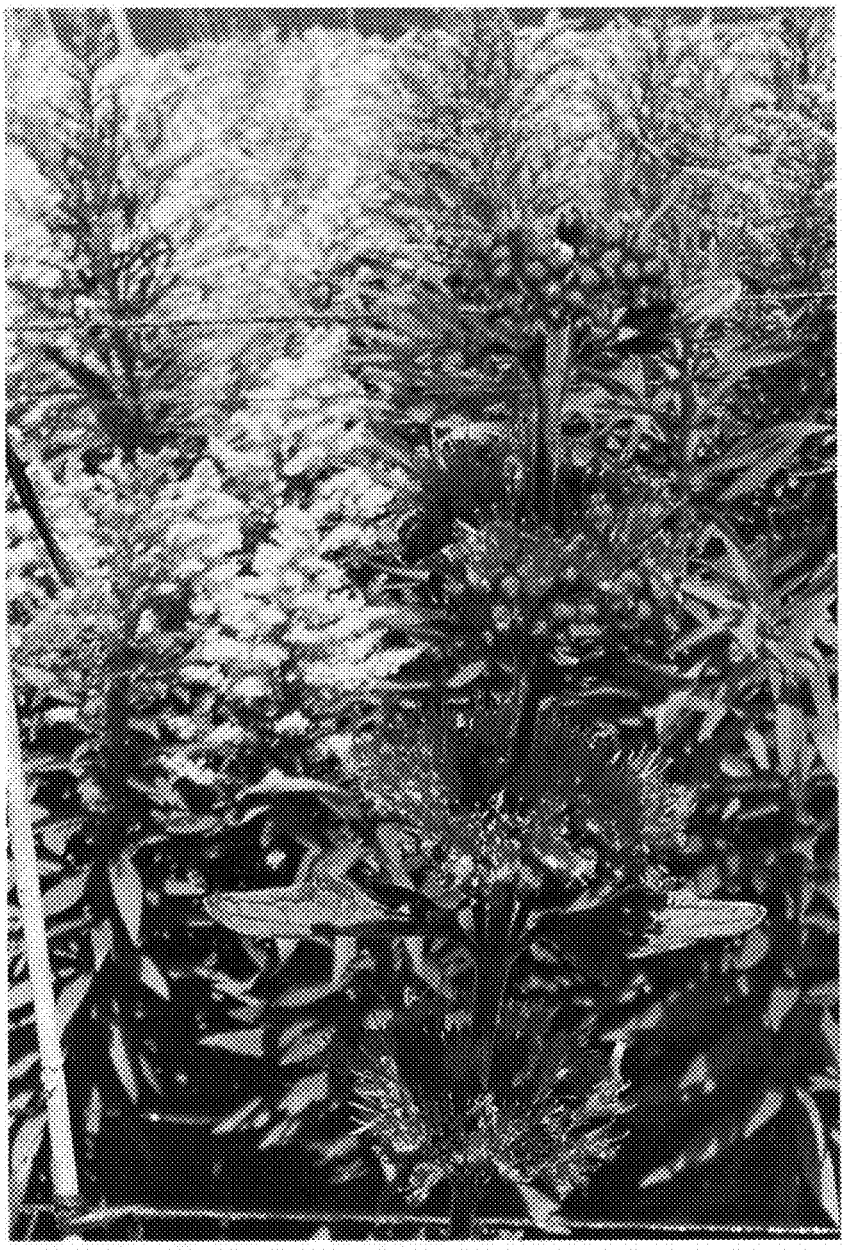

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Mini Chart 2005 except where general terms of ordinary dictionary significance are used. The following observations and measurements describe 'DCAROCEAN' plants grown outdoors during Spring and Summer in Moshav Mishmar Hashiva, Israel. The growing temperature ranged from approximately 20° C. to 35° C. during the day and from approximately 17° C. to 23° C. during the night. General light conditions are normal sunlight and numerical values represent averages of typical plant types.

Botanical classification: *Caryopteris incana* 'DCAROCEAN'.

PROPAGATION

Type of propagation typically used: Terminal vegetative cutting.

Time to initiate roots: About 7 days 20-25° C.

Time to produce a rooted cutting or liner: About 15-20 days at 20-25° C.

Root description: Fibrous system.

PLANT

Age of plant described: Approximately 18 weeks from rooted cutting.

Overall plant shape or growth habit: Upright.

Plant spread: Approximately 80-120 cm.

Plant height: Approximately 70-120 cm.

Growth rate: Medium.

Length of primary lateral branches: Approximately 75 cm.

Diameter of lateral branches: Between 0.3-0.6 cm.

Quantity of lateral branches: Between 10-15 branches.

*Color*.—Near Purple 79N-a RHS.

*Texture*.—Pubescent.

Internode length: Approximately 3 cm.

FOLIAGE

Leaf:

*Arrangement*.—Opposite.

*Quantity*.—Approximately 22 per main branch.

*Average length*.—Approximately 11 cm.

*Average width*.—Approximately 2.6 cm.

*Shape of blade*.—Lanceolate.

*Apex*.—Rounded.

*Base*.—Attenuate.

*Attachment*.—Absent.

*Margin*.—Crenate.

*Texture of top surface*.—Glabrous.

*Texture of bottom surface*.—Pubescent.

*Color*.—Young foliage upper side: Near Green 137N-c RHS. Young foliage under side: Near Green 138N-c RHS. Mature foliage upper side: Near Green 137N-a RHS. Mature foliage under side: Near Yellow-green 147-b RHS.

*Venation*.—Type: Anastomosing. Venation color upper side: Near Green 143-b RHS. Venation color under side: Near Yellow-green 144-d RHS.

*Petiole*.—Average Length: Approximately 1.9 cm. Diameter: Approximately 0.2 cm. Color: Near Yellow-green 144-a RHS with small variegation of near Red-purple 58-b RHS.

FLOWER

Natural flowering season: Late Summer, Autumn (Israel conditions).

Inflorescence type and habit: Axillary compound cymes.

Flower longevity on plant: Approximately 7 days.

Quantity of flowers: About 6-12 blooming spikes per each stem at the same time.

Inflorescence size:

*Diameter*.—Approximately 3.5 cm.

*Height*.—Approximately 3 cm.

*Flowers and buds per inflorescence*.—40-50.

Peduncle:

*Length*.—1.4 cm.

*Diameter*.—0.1 cm.

*Texture*.—Pubescent.

*Color*.—Near Yellow-green 144-b RHS.

*Orientation*.—Upright.

*Strength*.—Very elastic and strong.

Individual flowers:

*Petal arrangement*.—Zygomorphic with bilabiate petal.

*Arrangement*.—Simple.

*Size*.—

*Diameter*.—Approximately 0.5 cm.

*Length*.—Approximately 0.8 cm.

*Persistence*.—Non-persistent.

*Fragrance*.—Little.

Petals:

*Margin*.—Entire.

*Tip shape*.—Upper lip: Acute. Lower lip: Spacious dentate.

*Length*.—Upper lip: 0.2 cm. Lower lip: 0.45 cm. Tube: 0.15 cm.

*Width*.—Upper lip: 0.1 cm. Lower lip: 0.2 cm. Tube: 0.1 cm.

*Texture*.—Upper lip: Glaborus. Lower lip: Glaborus. Tube: Glaborus.

Color:

*Upper lip*.—When opening: Inner surface: Near Violet 88N-b RHS. Outer surface: Near Violet 87N-b RHS. Fully opened: Inner surface: Near Violet 87N-a RHS. Outer surface: Near Violet 86c RHS. Fading: Inner surface: Near Violet-blue 90c RHS. Outer surface: Near Violet-blue 90b RHS.

Color:

*Lower lip*.—When opening: Inner surface: Near Violet 88N-b RHS. Outer surface: Near Violet 87N-b RHS. Fully opened: Inner surface: Near Violet 87N-a RHS. Outer surface: Near Violet 86d RHS. Fading: Inner surface: Near Violet-blue 90b RHS. Outer surface: Near Violet 87N-a RHS.

Color:

*Tube*.—When opening: Inner surface: Near Violet-blue 91a RHS. Outer surface: Near Violet-blue 91b RHS. Fully opened: Inner surface: Near Violet 85b RHS. Outer surface: Near Violet 85c RHS. Fading: Inner surface: Near Violet 85c RHS. Outer surface: Near Violet 85c RHS.

Bud:

*Shape*.—Ellipse.
*Length*.—Approx. 0.1 cm.
*Diameter*.—Approx. 0.15 cm.
*Color*.—Near Violet 85d RHS.

Sepals:

*Shape*.—Linear.
*Quantity per flower*.—5.
*Length*.—Approximately 0.3 cm.
*Width*.—Approximately 0.15 cm.
*Margin*.—Entire.
*Texture*.—Pubescent.
*Color*.—Near Green 138b RHS.

REPRODUCTIVE ORGANS

Stamens:

*Number*.—4 stamen per flower.
*Filament length*.—Approximately 0.5 cm.

Anthers:

*Shape*.—Basifixed.
*Length*.—Less than 0.05 cm.
*Color*.—Near Violet-blue 95a RHS.
*Pollen*.—Color: Near Violet-blue 95b RHS. Quantity: Abundant.

Pistil:

*Number*.—1 per flower.
*Length*.—Approximately 0.6 cm.
*Style*.—Length: Approximately 0.55 cm. Color: Near Violet 85c RHS.
*Stigma*.—Shape: Lobed. Color: Near Violet 88N-b RHS. Ovary color: Near Green 135c RHS.

OTHER CHARACTERISTICS

Disease/pest resistance: Neither resistance nor susceptibility to normal diseases of *Caryopteris*. Typical pathogens include Prodenia and *Botrytis*. Typical pests include various Aphid and mite species.

Temperature tolerance: −26° C. lowest temperature tolerant, likely to tolerate colder. Highest temperature tolerant to 35° to 40° C.

Garden performance: Low maintenance, needs well drained soil.

What is claimed is:

1. A new and distinct cultivar of *Caryopteris* plant named 'DCAROCEAN' as herein illustrated and described.

* * * * *